United States Patent [19]

Lesher et al.

[11] 4,377,585
[45] Mar. 22, 1983

[54] USE OF 4-[4(OR 3)-AMINOPHENYL]PYRIDINES AS CARDIOTONIC AGENTS

[75] Inventors: George Y. Lesher, Schodack; Donald F. Page, East Greenbush, both of N.Y.

[73] Assignee: Sterling Drug Inc., New York, N.Y.

[21] Appl. No.: 284,771

[22] Filed: Jul. 20, 1981

Related U.S. Application Data

[62] Division of Ser. No. 152,991, May 27, 1980, Pat. No. 4,317,827.

[51] Int. Cl.$^3$ .............................................. A61K 31/44
[52] U.S. Cl. ..................................... 424/263; 546/300; 546/329
[58] Field of Search ........................ 424/263; 546/300; 546/329

[56] References Cited

U.S. PATENT DOCUMENTS 375,399 3/1973 Lesher et al. ........................ 546/156
390,780 8/1975 Lesher et al. ........................ 546/156
411,855 7/1978 Lesher ................................ 542/420

OTHER PUBLICATIONS

Heilbron et al., [J. Chem. Soc. *1940*, 1279].

*Primary Examiner*—Alan L. Rotman

*Attorney, Agent, or Firm*—Robert K. Bair; B. Woodrow Wyatt

[57] ABSTRACT

Disclosed and claimed are a cardiac composition and a method for increasing cardiac contractility using an effective amount of a cardiotonic 4-[4-(or 3)-AcNH-phenyl]-2-$R_2$-3-$R_3$-5-$R_5$-6-$R_6$-pyridine (I) or pharmaceutically-acceptable salt thereof, where $R_2$ is hydrogen, methyl, ethyl or hydroxyl, $R_6$ is hydrogen, methyl or ethyl, $R_3$ and $R_5$ are each hydrogen or methyl, and Ac is hydrogen, hydroxyacetyl, acetoxyacetyl, α-hydroxypropionyl, α-acetoxypropionyl, methyoxyacetyl, 2-butenoyl or carbamyl or when NHAc is attached to the 4-position of the phenyl ring Ac also is formyl, n-propanoyl, 2,2-dimethyl-n-propanoyl or 3-carboxypropanoyl or when NHAc is attached to the 3-position of the phenyl ring Ac also is acetyl. Novel compounds shown and claimed are 4-[4-(or 3)-Ac'NH-phenyl]-2-$R_2$-3-$R_3$-5-$R_5$-6-$R_6$-pyridines (II) or pharmaceutically-acceptable acid-addition salts thereof, where $R_2$, $R_3$, $R_5$ and $R_6$ are defined as above for I and Ac' is hydroxyacetyl, acetoxyacetyl, α-hydroxypropanoyl, α-acetoxypropionyl, methoxyacetyl, 2-butenoyl or carbamyl or where Ac'NH is attached to the 4-position of the phenyl ring Ac' is formyl, n-propanoyl, 2,2-dimethyl-n-propanoyl or 3-carboxypropanoyl. Also disclosed and claimed is the process for preparing said novel compounds (II).

3 Claims, No Drawings

USE OF 4-[4(OR 3)-AMINOPHENYL]PYRIDINES AS CARDIOTONIC AGENTS

CROSS-REFERENCE TO RELATED APPLICATION

This application is a division of copending application Ser. No. 152,991, filed May 27, 1980 and now U.S. Pat. No. 4,317,827, issued Mar. 2, 1982.

BACKGROUND OF THE INVENTION (a) Field of the Invention

This invention relates to cardiotonic compositions and method for increasing cardiac contractility using 4-[4(or 3)-aminophenyl]pyridines or acyl derivatives thereof, and to certain 4-[4(or 3)-acylaminophenyl]pyridines and their preparation.

(b) Description of the Prior Art

Heilbron et al [J. Chem. Soc. 1940, 1279] show as intermediates in the preparation of 3- and 4-pyridyldiphenyls the following compounds: β-3-aminophenylpyridine, β-4-aminophenylpyridine and γ-4-aminophenylpyridine and the N-acetyl derivatives of each, including the hydrochloride salt of β-4-acetamidophenylpyridine; these three aminophenylpyridines currently are named 3-(3-pyridinyl)benzeneamine, 4-(3-pyridinyl)benzeneamine and 4-(4-pyridinyl)benzeneamine, respectively.

Lesher and Carabateas [U.S. Pat. Nos. 3,753,993 (8-21-73) and 3,907,808 (9-23-75)] show as intermediates for making quinoline antibacterial agents various 3-(substituted-pyridinyl)benzeneamines where pyridinyl is substituted, inter alia, by lower-alkyl, hydroxyl, etc., illustrated by, 3-(2-methyl-4-pyridinyl)benzeneamine, 3-(2-hydroxy-6-methyl-4-pyridinyl)benzeneamine, 3-(2,6-dimethyl-4-pyridinyl)benzeneamine, 3-(2,6-diethyl-4-pyridinyl)benzeneamine, 3-(2,5-dimethyl-4-pyridinyl)benzeneamine, 3-(3-methyl-4-pyridinyl)benzeneamine, 3-(2-ethyl-4-pyridinyl)benzeneamine, and 3-(2,3-dimethyl-4-pyridinyl)benzeneamine.

Lesher [U.S. Pat. No. 4,118,557, issued Oct. 3, 1978] shows N-(lower-alkanoyl)derivatives of various 3-(pyridinyl)benzeneamines, as illustrated as follows: N-acetyl, N-formyl, N-propanoyl, N-butanoyl and N-hexanoyl derivatives of 3-(4-pyridinyl)benzeneamine; and, the N-acetyl derivatives of 3-(2-methyl-4-pyridinyl)benzeneamine, 3-(3-pyridinyl)benzeneamine, 3-(2,6-dimethyl-4-pyridinyl)benzeneamine and 3-(2-ethyl-4-pyridinyl)benzeneamine.

SUMMARY OF THE INVENTION

A composition aspect of the invention relates to a cardiotonic composition for increasing cardiac contractility in a patient, said composition comprising a pharmaceutically-acceptable carrier and, as the active component thereof, the cardiotonic 4-[4(or 3)-AcNH-phenyl]pyridine where Ac is hydrogen or selected acyl, or pharmaceutically-acceptable acid-addition salt thereof.

In a method aspect, the invention relates to a method for increasing cardiac contractility in a patient requiring such treatment which comprises the administration of a medicament comprising a pharmaceutically-acceptable carrier and, as the active component thereof, the cardiotonic 4-[4(or 3)-AcNH-phenyl]pyridine, where Ac is hydrogen or selected acyl, or pharmaceutically-acceptable acid-addition salt thereof.

In a composition of matter aspect, the invention relates to a novel 4-[4(or 3)-Ac'-aminophenyl]pyridine, where Ac' is a particularly selected acyl group, or pharmaceutically-acceptable acid-addition salt thereof.

In a process aspect, the invention resides in the process of producing certain novel 4-[4(or 3)-Ac'-aminophenyl]pyridine which comprises reacting 4-[4(or 3)-aminophenyl]pyridine with an acylating agent providing Ac', where Ac' is a particularly selected acyl group as defined hereinbelow.

DETAILED DESCRIPTION INCLUSIVE OF PREFERRED EMBODIMENTS

A composition aspect of the invention resides in a cardiotonic composition for increasing cardiac contractility, said composition comprising a pharmaceutically-acceptable inert carrier and, as the active component thereof, an effective amount of a cardiotonic 4-[4(or 3)-AcNH-phenyl]-2-$R_2$-3-$R_3$-5-$R_5$-6-$R_6$-pyridine having formula I

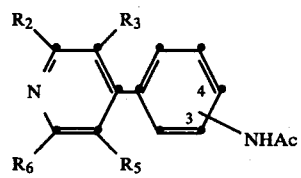

where $R_2$ is hydrogen, methyl, ethyl or hydroxyl, $R_6$ is hydrogen, methyl or ethyl, $R_3$ and $R_5$ are each hydrogen or methyl, and Ac is hydrogen, hydroxyacetyl, acetoxyacetyl, α-hydroxypropionyl, α-acetoxypropionyl, methoxyacetyl, 2-butenoyl or carbamyl or when NHAc is attached to the 4-position of the phenyl ring Ac also is formyl, n-propanoyl, 2,2-dimethyl-n-propanoyl or 3-carboxypropanoyl or when NHAc is attached to the 3-position of the phenyl ring Ac also is acetyl, or pharmaceutically-acceptable acid-addition salt thereof. Preferred embodiments of are those compositions where the active component is defined as above having $R_2$ as hydrogen, methyl, ethyl or hydroxyl, $R_3$, $R_5$ and $R_6$ are each hydrogen or methyl, and Ac is hydrogen, formyl only where NHAc is attached to the 4-position of the phenyl ring, hydroxyacetyl, α-hydroxypropionyl or carbamyl, or pharmaceutically-acceptable salt thereof.

A method aspect of the invention resides in the method for increasing cardiac contractility in a patient requiring such treatment which comprises administering orally or parenterally in a solid or liquid dosage form to such patient an effective amount of a cardiotonic 4-[4(or 3)-AcNH-phenyl]-2-$R_2$-3-$R_3$-5-$R_5$-6-$R_6$-pyridine having formula I where $R_2$, $R_3$, $R_5$, $R_6$ and Ac are defined as hereinabove for the cardiotonic composition, or pharmaceutically-acceptable acid-addition salt thereof. Preferred embodiments of this aspect of the invention uses said cardiotonic where $R_2$ is hydrogen, methyl, ethyl or hydroxyl, $R_3$, $R_5$ and $R_6$ are each hydrogen or methyl, and Ac is hydrogen, formyl only where NHAc is attached to the 4-position of the phenyl ring, hydroxyacetyl, α-hydroxypropionyl, methoxyacetyl or carbamyl, or pharmaceutically-acceptable acid-addition salt thereof.

In a composition of matter aspect, the invention resides in 4-[4(or 3)-Ac'-NH-phenyl]-2-$R_2$-3-$R_3$-5-$R_5$-6-$R_6$-pyridine having the formula II

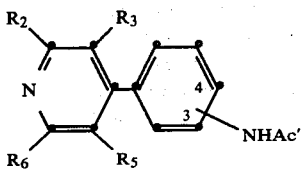

II where $R_2$ is hydrogen, methyl, ethyl or hydroxyl, $R_6$ is hydrogen, methyl or ethyl, $R_3$ and $R_5$ are each hydrogen or methyl, and Ac' is hydroxyacetyl, acetoxyacetyl, α-hydroxypropionyl, α-acetoxypropionyl, methoxyacetyl, 2-butenoyl or carbamyl or when NHAc' is attached to the 4-position of the phenyl ring Ac' also is formyl, n-propanoyl, 2,2-dimethyl-n-propanoyl or 3-carboxypropanoyl, or pharmaceutically-acceptable acid-addition salt thereof. Preferred embodiments of this aspect of the invention are the compounds where $R_2$ is hydrogen, methyl, ethyl or hydroxyl, $R_3$, $R_5$ and $R_6$ are each hydrogen or methyl, and Ac' is hydroxyacetyl, α-hydroxypropionyl, carbamyl or where NHAc' is attached to the 4-position of the phenyl ring Ac' is formyl or n-propanoyl, or pharmaceutically-acceptable acid-addition salt thereof.

The invention in a process aspect resides in the process of reacting 4-[4(or 3)-aminophenyl]-2-$R_2$-3-$R_3$-5-$R_5$-6-$R_6$-pyridine with an acylating agent providing Ac' to produce 4-[4(or 3)-Ac'-aminophenyl]-2-$R_2$-3-$R_3$-5-$R_5$-6-$R_6$ pyridine where Ac', $R_2$, $R_3$, $R_5$ and $R_6$ have the meanings given above for formula II.

The compounds of formulas I and II are useful both in the free base form and in the form of acid-addition salt, and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial cardiotonic properties inherent in the free base are not vitiated by side effects ascribable to the anions. In practicing the invention, it is convenient to use the hydrochloride or the lactate. However, other appropriate pharmaceutically-acceptable salts within the scope of the invention are those derived from mineral acids such as hydrobromic acid, sulfuric acid, phosphoric acid and sulfamic acid; and organic acid such as acetic acid, citric acid, tartaric acid, methanesulfonic acid, ethanesulfonic acid, benzenesulfonic acid, p-toluenesulfonic acid, cyclohexylsulfamic acid, quinic acid, and the like, giving the hydrobromide, sulfate, phosphate, sulfamate, acetate, citrate, tartrate, methanesulfonate, ethanesulfonate, benzenesulfonate, p-toluenesulfonate, cyclohexylsulfamate and quinate respectively.

The acid-addition salts of the compounds of formulas I and II are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically-acceptable salts of said compounds of formulas I and II are preferred, all acid-addition salts are within the scope of our invention. All acid-addition salts are useful as sources of the free base form even if the particular salt per se is desired only as an intermediate product, as for example when the salt is formed only for purposes of purification or identification, or when it is used as an intermediate in preparing a pharmaceutically-acceptable salt by ion exchange procedures.

The molecular structures of the novel compounds of formula II were assigned on the basis of evidence provided by infrared, nuclear magnetic resonance and mass spectra, and by the correspondence of calculated and found values for the elemental analysis.

The manner of making and using the instant invention will now be generally described so as to enable a person skilled in the art of pharmaceutical chemistry to make and use the same, as follows.

The reaction of 4-[4(or 3)-aminophenyl]-2-$R_2$-3-$R_3$-5-6-$R_6$-pyridine with an acylating agent providing Ac' to produce 4-[4(or 3)-Ac'-aminophenyl]-2-$R_2$-3-$R_3$-5-$R_5$-6-$R_6$-pyridine of formula II is carried out using various acylating agents, viz., heating directly with formic acid or heating with an acid in benzene, toluene or xylene in a flask equipped with a water separator, heating the acid with an anhydride in a suitable solvent or reacting an acid chloride in an inert solvent, viz., chloroform, methylene dichloride, pyridine, etc., in the presence of an acid-acceptor, e.g., pyridine, $K_2CO_3$, etc., preferably at about 0° to 5° C. These acylations are illustrated further hereinbelow.

The following examples will further illustrate the invention without, however, limiting it thereto.

EXAMPLE 1

N-[4-(4-Pyridinyl)phenyl]formamide

A mixture containing 11.1 g. of 4-(4-pyridinyl)benzeneamine and 150 ml. of 97% formic acid was stirred under reflux over 2½ hours and the mixture was then concentrated in vacuo. The residue was suspended in water, the mixture was made alkaline with ammonium hydroxide solution and the solid was collected, washed with water and recrystallized from ethanol to yield 4.4 g. of product, m.p. 186°–188° C. A second crop of product weighing 3.9 g. was obtained by concentrating the filtrate; and, a third crop weighing 1.4 g. was isolated by concentrating the second filtrate. The first two crops were combined and the mixture was recrystallized from isopropyl alcohol and dried at 80° C. in a vacuum oven for 18 hours to yield 7 g. of N-[4-(4-pyridinyl)phenyl]-formamide, m.p. 188°–190° C. In another run following the above procedure in using 13.6 g. of 4-(4-pyridinyl)-benzeneamine, 175 ml. of 97% formic acid and a reflux period of over 4½ hours. The residue, after concentration of the reaction mixture in vacuo, was taken up in 300 ml. of water, the aqueous mixture was treated with decolorizing charcoal and filtered and the aqueous acidic filtrate was made alkaline with ammonium hydroxide solution and chilled. The separated solid was boiled in isopropyl alcohol to remove the water; the solution concentrated to 200 ml.; and, a slight excess of hydrogen chloride in ethanol was added to the partly cooled solution. The suspension was diluted with ether to ensure complete precipitation of the product. The precipitate was collected and dried at 80° C. in a vacuum oven for 16 hours to produce 17.2 g. of N-[4-(4-pyridinyl)phenyl]formamide hydrochloride, m.p. 249°–250.5° C. with decomposition.

EXAMPLE 2

2-Methoxy-N-[4-(4-pyridinyl)phenyl]acetamide

A mixture containing 12.8 g. of 4-(4-pyridinyl)benzeneamine, 17.2 ml. of methoxyacetic acid and 250 ml. of xylene was refluxed with stirring over 12 hours in a flask equipped with a condenser and a water separator. The reaction mixture was then concentrated in vacuo and the residue was suspended in water and the mixture made alkaline with potassium carbonate solution. The tan solid was collected, dissolved in hot isopropyl alcohol, the hot solution filtered to remove a small amount of insoluble material and the filtrate allowed to cool. The separated solid was collected, dried in vacuo at 90° C. over 18 hours to yield 13.7 g. of 2-methoxy-N-[4-(4-pyridinyl)phenyl]acetamide, m.p. 177°-178.5° C.

EXAMPLE 3

N-[4-(4-pyridinyl)phenyl]urea

A 39.2 g. portion of 4-(4-pyridinyl)benzeneamine was dissolved in 150 ml. of warm acetic acid and 230 ml. of water was added. The solution was stirred and warmed to 55° C. on a steam bath and then a warm solution containing 74.1 g. of potassium cyanate in 460 ml. of water was added dropwise over a period of 1 hour using a dropping funnel with a long stem which dipped well below the surface of the reaction mixture. The reaction temperature was maintained at 55°-60° C. throughout the addition. A yellow solid began to form after about ⅓ of the potassium cyanate had been added. The reaction mixture was allowed to cool with continued stirring for about 30 minutes and then was allowed to stand for 2 hours. To the stirred solution was added concentrated ammonium hydroxide (about 60 ml.) to a pH of 8. The mixture was cooled well in an ice bath and the separated solid was collected, washed well with fresh water and sucked as dry as possible. The damp solid was recrystallized from 400 ml. of dimethylformamide using decolorizing charcoal and the recrystallized material was collected, washed with ethanol and dried in a vacuum oven at 60° C. to produce 19.3 g. of N-[4-(4-pyridinyl)phenyl]urea, m.p. 245°-247° C.

EXAMPLE 4

2-Hydroxy-N-[4-(4-pyridinyl)phenyl]propanamide

A mixture containing 10.2 g. of 4-(4-pyridinyl)benzeneamine, 18.8 g. of 80% lactic acid and 300 ml. of xylene was refluxed with stirring for over 1¾ hours in a flask equipped with a condenser and water separator. The resulting suspension was concentrated in vacuo, the residue was treated with water and the aqueous mixture was made alkaline with 10% potassium carbonate solution. The solid was collected, washed with water and recrystallized from isopropyl alcohol (final volume of 100 ml.). Drying the resulting solid at 90° C. in a vacuum oven for 16 hours produced 6.24 g. of 2-hydroxy-N-[4-(4-pyridinyl)phenyl]propanamide, m.p. 236°-238° C.

Following the procedure described below in Example 10 but using in place of 3-methylbutanoic acid chloride a molar equivalent quantity of 2-acetoxypropanoyl chloride, it is contemplated that there can be obtained 2-acetoxy-N-[4-(4-pyridinyl)phenyl]propanamide.

EXAMPLE 5

2-Hydroxy-N-[4-(4-pyridinyl)phenyl]acetamide

A mixture containing 15 g. of 4-(4-pyridinyl)benzeneamine, 28.25 g. of 70% glycolic acid and 250 ml. of xylene was refluxed for over 4 hours with stirring in a flask equipped with a condenser and water separator. The reaction mixture was concentrated in vacuo; the residue was stirred with 250 ml. of water; and, the aqueous mixture was made alkaline with potassium carbonate solution. The solid was collected, recrystallized from isopropyl alcohol (final volume of 250 ml.) and dried at 90° C. in a vacuum oven for 18 hours to yield 13.8 g. of 2-hydroxy-N-[4-(4-pyridinyl)phenyl]acetamide, m.p. 231°-234° C. A second crop of 1.39 g. of product was obtained. Combined crops were recrystallized from acetonitrile (final volume 1500 ml.) and the product dried at 180° C. in vacuo over 16 hours. The recrystallized product was dissolved in 300 ml. of dimethylformamide and the solution treated with a slight excess of hydrogen chloride in ethanol. The suspension was diluted with ether and the precipitated product was collected and dried in a vacuum oven for 16 hours at 125° to yield 16.88 g. of 2-hydroxy-N-[4-(4-pyridinyl)phenyl]acetamide hydrochloride, m.p. 270°-274° C.

Following the procedure described below in Example 10 but using in place of 3-methylbutanoic acid chloride a molar equivalent quantity of acetoxyacetyl chloride, it is contemplated that there can be obtained 2-acetoxy-N-[4-(4-pyridinyl)phenyl]acetamide.

EXAMPLE 6

N-[4-(4-Pyridinyl)phenyl]propanamide

An 8.51 g. portion of 4-(4-pyridinyl)benzeneamine was added to a solution containing 38.8 ml. of propanoic acid anhydride in 100 ml. of chloroform and dissolution was incomplete after 24 hours at room temperature. The reaction mixture was then stirred under reflux for 8 hours and the warm suspension was filtered through diatomaceous earth and the filtrate was concentrated in vacuo. The residue was suspended in water, the mixture was made basic with ammonium hydroxide solution and the solid was collected and washed with water. The solid was taken up in 150 ml. of hot isopropyl alcohol and to the solution was added 250 ml. of hot water. The resulting solution was filtered and then allowed to cool whereupon there separated an oil which crystallized on standing. The crystalline material was collected and dried in vacuo at 80° C. for 80 hours to yield 10.66 g. of N-[4-(4-pyridinyl)phenyl]propanamide, m.p. 179°-181° C.

EXAMPLE 7

2,2-Dimethyl-N-[4-(4-pyridinyl)phenyl]propanamide

To a mixture containing 8.51 g. of 4-(4-pyridinyl)benzeneamine suspended in 100 ml. of ethylene chloride with stirring a solution containing 13.27 g. of potassium carbonate in 60 ml. of water. To the resulting suspension chilled to about 5° C. was added over a 20 minute period with stirring a solution containing 4.7 g. of 2,2-dimethylpropanoyl chloride in 40 ml. of ethylene chloride and stirring was continued in the cold for about 4 hours and then with no external cooling for about 16 hours. The suspension was filtered and the layers in the filtrate were separated. The ethylene chloride layer was concentrated in vacuo to leave a orange-yellow solid.

Since the acylation of the insoluble pyridinyl benzeneamine was incomplete, the above filter cake from the reaction mixture was taken up in isopropyl alcohol and the solution was concentrated in vacuo to remove the alcohol and water. The residue was combined with the above orange-yellow solid obtained from the ethylene dichloride layer and together in 125 ml. of pyridine chilled in an ice bath was added with stirring over a ten minute period a solution containing 4.7 g. of 2,2-dimethylpropanoyl chloride in 20 ml. of ethylene chloride. The reaction mixture was stirred with cooling for another hour and then for 90 minutes without cooling. The reaction mixture was concentrated in vacuo to a volume of less then 100 ml. and was dropped into 300 ml. of water containing an excess of 2 N potassium hydroxide solution. The precipitated solid was recrystallized from 100 ml. of isopropyl alcohol, dried in vacuo at 90° C. for over 3 hours and then dissolved in 150 ml. of methanol and the resulting solution treated with excess hydrogen chloride in ethanol. To the resulting mixture was added chloroform and the separated product was collected and dried in vacuo at 90° C. for 16 hours to yield 8.67 g., as yellow-tan prisms, 2,2-dimethyl-N-[4-(4-pyridinyl)phenyl]propanamide as its hydrochloride, m.p. 277°–282° C. Another 1.30 g. of the product, m.p. 274°–279° C., was obtained from the mother liquor.

EXAMPLE 8

4-Oxo-4-[4-(4-pyridinyl)phenylamino]butanoic Acid

A mixture containing 50 g. of 4-(4-pyridinyl)benzeneamine, 32 g. of succinic anhydride and 1 liter of chloroform was stirred under reflux for 10 hours and then filtered. The filtrate on cooling yielded a yellow crystalline product which was collected and dried in vacuo at 90° C. for 16 hours to yield 77.2 g. of product, m.p. 251°–251.5° C. A 10 g. portion of this product was recrystallized from 200 ml. of acetic acid, the hot solution being filtered and the filtrate being allowed to cool to room temperature. The separated solid was collected and dried in vacuo at 90° C. over sodium hydroxide for 16 hours to yield 4.57 g. of 4-oxo-4-[4-(4-pyridinyl)phenylamino]butanoic acid, m.p. 256°–257° C.

EXAMPLE 9

N-[4-(4-pyridinyl)phenyl]-2-butenamide

A mixture containing 6.8 g. of 4-(4-pyridinyl)benzeneamine, 17.8 ml. of crotonic anhydride and 200 ml. of chloroform was stirred at room temperature for 2 hours and then under reflux for 16 hours. The suspension was filtered and the filtercake was suspended in water plus ammonium hydroxide solution and was refiltered to give 3.86 g. of light tan solid after air-drying on the funnel. The chloroform filtrate was concentrated in vacuo and the tan residue was suspended in a mixture of water and ammonium hydroxide and the mixture filtered to give more tan solids. The combined tan solids were taken up in dimethylformamide, the hot solution filtered and the filtrate concentrated to less than 300 ml. and then treated with a slight excess of methanesulfonic acid in ethanol. The resulting mixture was diluted with ether and the separated product was collected and dried in vacuo at 125° C. for 14 hours to yield 4.31 g. of N-[4-(4-pyridinyl)phenyl]-2-butenamide methanesulfonate, m.p. 247°–249° C.

The following examples 10 and 11 show the preparation of two novel N-acyl derivatives of 4-(4-pyridinyl)benzeneamine which are not useful as cardiotonic agents and thus are not within the scope of the claims in the instant application; these examples are included herein for comparative purposes as seen hereinbelow under discussion of cardiotonic activity of the useful cardiotonics covered by the instant claims.

EXAMPLE 10

3-Methyl-N-[4-(4-pyridinyl)phenyl]butanamide

To 8.51 g. of 4-(4-pyridinyl)benzeneamine in 125 ml. of pyridine chilled in an ice bath was added with stirring over a ten minute period a solution containing 7.72 g. of 3-methylbutanoic acid chloride in 25 ml. of ethylene chloride. The resulting mixture was stirred with cooling in the ice bath for about 90 minutes and then at room temperature for about 16 hours. The reaction mixture was then heated on a steam bath for 90 minutes and filtered hot through diatomaceous earth. The filtrate was diluted with water and then made alkaline with ammonium hydroxide solution. When there separated only an oily material, the mixture was concentrated in vacuo and the resulting tan solid was collected, washed with dilute ammonium hydroxide solution and then with water. The solid was recrystallized from 150 ml. of isopropyl alcohol and the solution diluted with aqueous ammonium hydroxide. The separated solid was collected and dried in vacuo at 90° C. for 20 hours to yield 10.52 g. of 3-methyl-N-[4-(4-pyridinyl)phenyl]butanamide, m.p. 166°–176° C. This compound was dissolved in 250 ml. of methanol and the solution treated with excess hydrogen chloride in ethanol, followed by dilution with ether. The precipitated product was collected and dried at 85° C. in vacuo for 60 hours to yield 8.2 g. of 3-methyl-N-[4-(4-pyridinyl)phenyl]butanamide hydrochloride, m.p. 257°–264° C.

EXAMPLE 11

N-[4-(4-Pyridinyl)phenyl]butanamide

To a mixture containing 19.6 g. of n-butanoic acid anhydride in 150 ml. of chloroform was added with stirring 6.81 g. of 4-(4-pyridinyl)benzeneamine and the resulting mixture was stirred at room temperature for 17 hours and then refluxed with stirring for 90 minutes. The reaction mixture while warm was filtered through diatomaceous earth and the filtrate was concentrated on a steam bath to remove the solvent. The residue was diluted with water, the aqueous mixture made alkaline with ammonium hydroxide and the resulting mixture was stirred, concentrated further to remove small amount of remaining chloroform and the resulting solid was collected. The solid was recrystallized from 150 ml. of ethanol plus water and dried in vacuo at 90° C. for 20 hours to yield 8.2 g. of N-[4-(4-pyridinyl)phenyl]butanamide, m.p. 174°–175° C. This compound was then dissolved in 250 ml. of methanol and the solution treated with an excess of hydrogen chloride in ethanol and the resulting mixture diluted with ether. The separated product was collected, dried at 80°–85° C. in vacuo for 60 hours to yield 8.79 g. of N-[4-(4-pyridinyl)phenyl]butanamide hydrochloride, m.p. 289°–293° C.

The usefulness of the compounds of formulas I and II or salts thereof as cardiotonic agents is demonstrated by their effectiveness in standard pharmacological test procedures, for example, in causing a significant increase in contractile force of the isolated cat atria and papillary muscle and/or in causing a significant increase in the cardiac contractile force in the anesthetized dog with low or minimal changes in heart rate and blood pressure. Detailed descriptions of these test procedures appear in U.S. Pat. No. 4,072,746, issued Feb. 7, 1980.

When tested by said isolated cat atria and papillary muscle procedure, the compounds of formulas I and II or pharmaceutically-acceptable acid-addition salts thereof at doses of 10, 30, 100 and/or 300 µg/ml., were found to cause significant increases, that is, greater than 25% in papillary muscle force and significant increases, that is, greater than 25%, in right atrial force, while causing a lower percentage increase (about one-half or less than the percentage increase in right atrial force or papillary muscle force) in right atrial rate. For example, when tested at said dose levels by this procedure, the following compounds were found to cause increases of 50% and greater in papillary muscle force and/or right atrial force: the compounds of Examples 1, 2, 3, 4, 5, 6, 8 and 9. The preferred compounds of Examples 1, 2, 3, 4, 5 and 6, as well as Example 9, were found to cause increases of 100% and greater in papillary muscle force and/or right atrial force. Known compounds of Formula I found to cause papillary muscle force increases of 80% or greater at one or more of said doses when tested by said procedure are: 3-(4-pyridinyl)benzeneamine, 4-(4-pyridinyl)benzeneamine, 3-(2-ethyl-4-pyridinyl)benzeneamine, 3-(2,5-dimethyl-4-pyridinyl)benzeneamine, 3-(2,6-dimethyl-4-pyridinyl)benzeneamine, 3-(2-hydroxy-6-methyl-4-pyridinyl)benzeneamine and N-[3-(4-pyridinyl)phenyl]acetamide.

When tested by said anesthetized dog procedure, the compounds of formulas I and II or pharmaceutically-acceptable acid-addition salts thereof at doses of 1.0, 3.0 and/or 10 mg./kg. administered intravenously were found to cause significant increases, that is, 25% or greater, in cardiac contractile force or cardiac contractility with lower changes in heart rate and blood pressure. For example, when tested at said dose levels by this procedure, the following compounds were found to cause increases of 50% and greater in contractile force and lower changes in heart rate and blood pressure: the compounds of Examples 1-9 inclusive. The preferred compounds of Examples 1-6 inclusive were found to cause contractile force increases of 90% and greater at one or more of said dose levels in this test in the anesthetized dog. Known compounds causing a contractile force increase of 50% or greater in this test are 3-(4-pyridinyl)benzeneamine and 4-(4-pyridinyl)benzeneamine.

Compounds found unsatisfactory as cardiotonic agents when tested by one or both of the above-noted in vitro cat atria and in vivo anesthetized dog procedures include the compounds of Examples 10 and 11 as well as N-[3-(4-pyridinyl)phenyl]propionamide, N-[4-(4-pyridinyl)phenyl]acetamide and N-[3-(4-pyridinyl)phenyl]formamide.

When screened by other standard pharmacological test procedures, some embodiments of the compounds of formulas I and II or salts thereof were found to have antihypertensive activity. For example, the compounds of Examples 1, 7 and known 3-(2,6-dimethyl-4-pyridinyl)benzeneamine were found to have oral $AHD_{40}$ values of 50, 40 and 40 mg./kg. respectively when tested in the spontaneously hypertensive rat; similarly, the compounds of Examples 3 and 5 were found to have lower antihypertensive activities (32% and 35% reduction in pressure at 50 and 150 mg./kg. p.o. respectively) when tested by this procedure.

The present invention includes within its scope a cardiotonic composition for increasing cardiac contractility, said composition comprising a pharmaceutically-acceptable carrier and, as the active component thereof, the cardiotonic compound of formulas I or II or pharmaceutically-acceptable acid-addition salt thereof. The invention also includes within its scope the method for increasing cardiac contractility in a patient requiring such treatment which comprises administering to such patient an effective amount of cardiotonic compound of formula I or II or pharmaceutically-acceptable acid-addition salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions can also contain additional substances other that inert diluents, e.g., lubricating agents, such as magnesium stearate, talc and the like.

Liquid compositions for oral administration include pharmaceutically-acceptable emulsions, solutions, suspensions, syrups and elixirs containing inert diluents commonly used in the art, such as water and liquid paraffin. Besides inert diluents such compositions can also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilising, preserving, wetting, emulsifying and dispersing agents.

They can be sterilized, for example, by filtration through a bacteria-retaining filter, by incorporation of sterilising agents in the compositions, by irradiation or by heating. They can also be manufactured in the form of sterile solid compositions which can be dissolved in sterile water or some other sterile injectable medium immediately before use.

The percentages of active component in the said composition and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing the best judgement on the patient's behalf.

We claim:

1. The method for increasing cardiac contractility in a patient requiring such treatment which comprises administering orally or parenterally in a solid or liquid dosage form to such patient an effective amount of a cardiotonic 4-[4(or 3)-aminophenyl]-2-$R_2$-3-$R_3$-5-$R_5$-6-$R_6$-pyridine having the formula

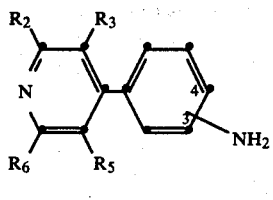

where $R_2$ is hydrogen, methyl, ethyl or hydroxyl, $R_6$ is hydrogen, methyl or ethyl, $R_3$ and $R_5$ are each hydrogen or methyl, or pharmaceutically-acceptable acid-addition salt thereof.

2. The method according to claim 1 where $R_2$ is hydrogen, methyl, ethyl or hydroxyl, and $R_3$, $R_5$ and $R_6$ are each hydrogen or methyl.

3. The method according to claim 1 where the cardiotonic is 4-(4-aminophenyl)pyridine or pharmaceutically-acceptable acid-addition salt thereof.

* * * * *